United States Patent [19]

Wearn

[11] Patent Number: 4,926,820
[45] Date of Patent: May 22, 1990

[54] DENTAL FLOSS HOLDING ASSEMBLY

[76] Inventor: E. Stafford Wearn, P.O. Box 1746, Statesville, N.C. 28677

[21] Appl. No.: 331,499

[22] Filed: Mar. 31, 1989

[51] Int. Cl.$^5$ ............................................. A61C 15/00
[52] U.S. Cl. .................................................. 132/323
[58] Field of Search ................ 132/323, 324, 325, 326

[56] References Cited

U.S. PATENT DOCUMENTS

| | | | |
|---|---|---|---|
| 1,174,016 | 2/1916 | Kenyon | 132/325 |
| 1,559,320 | 10/1925 | Hirsh | 132/323 |
| 3,881,502 | 5/1975 | Bennington | 132/325 |
| 4,016,892 | 4/1977 | Chodorow | 132/323 |
| 4,050,470 | 9/1977 | Miller | 132/325 |
| 4,151,851 | 5/1979 | Bragg | 132/326 |
| 4,622,986 | 11/1986 | Harris et al. | 132/324 |
| 4,638,824 | 1/1987 | De La Hoz | 132/323 |
| 4,729,392 | 3/1988 | Tenny | 132/323 |

FOREIGN PATENT DOCUMENTS 2122495 1/1984 United Kingdom ................ 132/323

Primary Examiner—John J. Wilson
Attorney, Agent, or Firm—W. Thad Adams, III

[57] ABSTRACT

A dental floss holding assembly comprising a pair of holders, one each for being held in a hand while dental floss suspended under tension therebetween is manipulated in dental interstices. Each of the pair of holders comprises a compact, hand-holdable member for being held in the palm of the hand, the member having positioned thereon an outwardly-extending disk defining a floss-retaining groove between the member and the disk for securing one wrapped end of the length of floss therearound. In another embodiment, a box holding a supply of floss is provided with a disk around which the floss is wrapped to hold in one hand.

8 Claims, 2 Drawing Sheets

FIG. 6
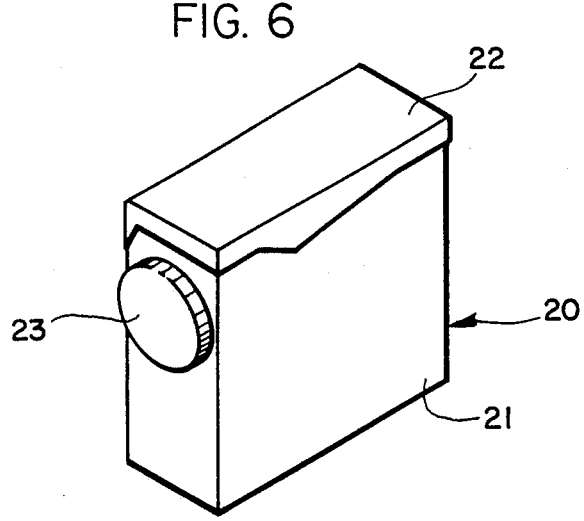
FIG. 7
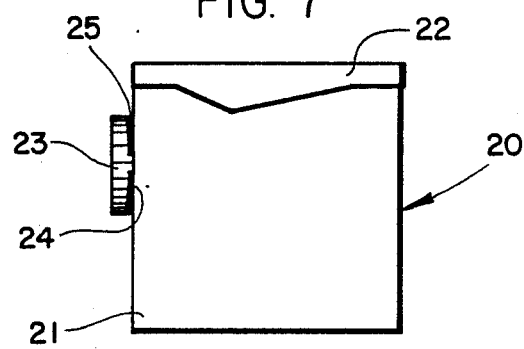
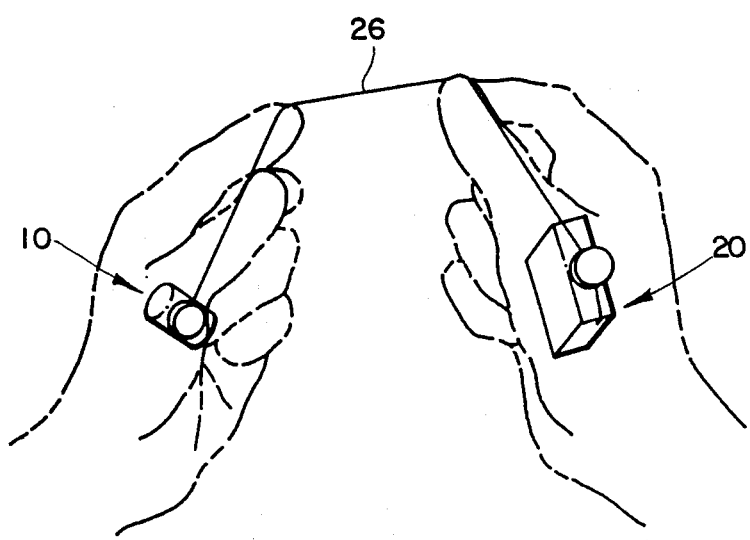
FIG. 8

DENTAL FLOSS HOLDING ASSEMBLY

TECHNICAL FIELD AND BACKGROUND OF THE INVENTION

This invention relates to a dental floss holding assembly which provides a convenient, comfortable, safe and sanitary means for facilitating the use of dental floss in a dental care program. Numerous types of floss holders are known. Some are unitary devices, typically with a "fork" between which the floss is held under tension. See U.S. Pat. No. 3,106,216 to Kirby, and No. 4,729,392 to Tenny. Others come in pairs and are held in the hand or are attached to the fingers. See, for example, U.S. Patent No. 1,559,320 to Hirsh, No. 4,016,892 to Chodorow and 4,638,824 to De La Hoz.

Insofar as applicant is aware, no prior art device provides a structure which can be easily held in the palm of the hand while permitting quick, secure and easy adjustment of the length of the floss. Furthermore, no such device is known which leaves the index fingers and thumbs free and unencumbered to manipulate the floss.

SUMMARY OF THE INVENTION

Therefore, it is an object of the invention to provide a safe, comfortable and easy to use dental floss holder.

It is another object of the invention to provide a dental floss holder which permits easy adjustment of the floss before, during and after use.

It is another object of the invention to provide a dental floss holder which leaves the index fingers and thumbs free to manipulate the floss.

It is another object of the invention to provide a dental floss holder which permits a supply length of floss to be stored in one of the holders.

It is another object of the invention to provide a dental floss holder which is very inexpensive.

These and other objects of the present invention are achieved in the preferred embodiments disclosed below by providing a dental floss holding assembly comprising a pair of holders, one each for being held in a hand while dental floss suspended under tension therebetween is manipulated in dental interstices. Each of the pair of holders comprises a compact, hand-holdable member for being held in the palm of the hand, the member having positioned thereon an outwardly-extending disk defining a flossretaining groove between the member and the disk for securing one wrapped end of the length of floss therearound.

According to one preferred embodiment of the invention, the pair of holders are identical.

According to another preferred embodiment of the invention, one of the members comprises a box with a disk attached on the outside containing a storage supply of dental floss therein for being dispensed in incremental use lengths as needed.

Preferably, the member and the disk are integrally-formed of a moldable plastic material.

According to one preferred embodiment of the invention, the member comprises a solid cylinder with a disk positioned on an axially-extending cylindrical side wall of the member at substantial right angles thereto.

Preferably, the disk has a diameter no greater or no less than the diameter of the member.

To facilitate the securement of the floss in the groove, the groove decreases in width towards the attachment of the disk on the cylinder.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 6 is perspective view of a holder according to another embodiment of the invention;

FIG. 7 is a side elevation of the holder shown in FIG. 6; and

FIG. 8 is a view showing the manner in which the holder shown in FIG. 1 and the holder shown in FIG. 6 are preferably held and the floss manipulated.

DESCRIPTION OF THE PREFERRED EMBODIMENT AND BEST MODE

Figure 1:
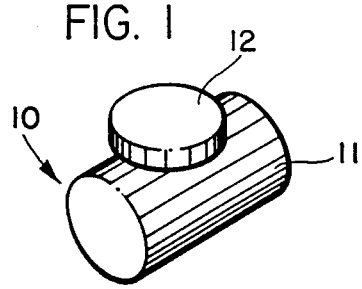
FIG. 1 is a perspective view of a holder according to the invention.

Referring now specifically to the drawings, a floss holder according to the present invention is illustrated in FIG. 1 and shown generally at reference numeral 10. Holder 10 comprises a solid, cylindrical member 11 preferably molded from a hard, nonbreakable plastic of a type which several well-known floss holders are currently constructed. This type of material is safe and sanitary for use by all ages. Member is sized to be comfortably held in the hand.

Figure 2:
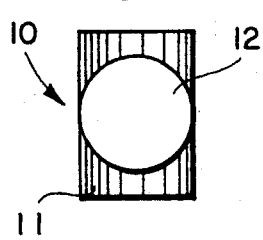
FIG. 2 is a top elevation of the holder shown in FIG. 1.

A disk 12 is preferably integrally-formed on one axiallyextending side wall of member 11. As is best shown in FIG. 2, the disk 12 is disk-shaped and preferably has a diameter substantially the same as the cylindrical member 11. Of course, many other sizes and relative proportions are possible.

Figure 3:
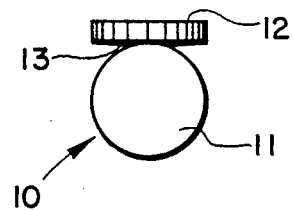
FIG. 3 is an end plan view of the holder shown in FIG. 1.
Figure 4:
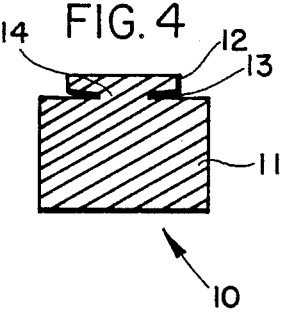
FIG. 4 is a vertical cross-section of the holder shown in FIG. 1.

As is shown in FIGS. 3 and 4, the bottom surface of disk 12 and the adjacent wall surface of member 11 define a space towards the center of disk 12 which serves as a floss-receiving annular groove 13. As is best shown in FIG. 4, Holder 10 is preferably a solid, one-piece structure, with the juncture between member 11 and disk 12 forming post 14 around which the floss is wrapped and secured. Groove 13 is slightly tapered towards post 14. This structure serves to force the floss tightly together into the groove 13 so that it is locked in position around post 14.

In an alternative embodiment, disk 13 may be a separate piece which is secured to the member 11 by suitable means. This embodiment is not illustrated.

Figure 5:
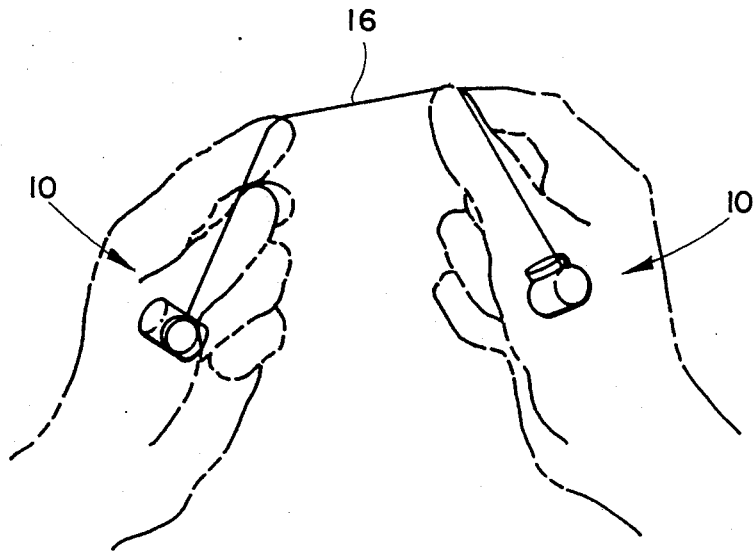
FIG. 5 is a view showing the manner in which the holders are preferably held and the floss manipulated.

Referring now to FIG. 5, use of the holder 10 is illustrated. A pair of holders 10 is secured together by a connecting piece of floss 16. The floss 16 is cut to sized to form a length, which, when wound two or three times around the posts 14 of holders 10, securely holds the floss 16. Some users may choose to wind a short supply length (enough for one or more uses) around one of the posts 14, dispensing a fresh length of floss periodically during a single cleaning by unwinding a short length of fresh floss from one holder and winding the just-used length of floss towards and eventually onto post 14 of the other holder. The length of floss 16 between holders 10 remains relatively the same.

The holders are held in the palm of the hands as shown in FIG. 5. The thumb and index finger of each hand is free to guide the floss 16 between the teeth.

Another embodiment of the invention is shown in FIGS. 6-8. In accordance with this embodiment of the invention, a single holder 10 is used, being held in one hand, with a holder 20 as shown in FIGS. 6 and 7 being held in the other. Holder 20 comprises a plastic box 21 within which is contained a reel or spool of floss, not shown. A plastic lid 22 normally encloses box 21 and is hinged to permit a use length of floss to be removed. Preferably, lid 22 is integrally-formed with box 21.

A disk 23 is integrally-formed on the outside of the box 21. The bottom surface of the disk 24 cooperates with the adjacent side wall of box 21 to define a groove 25 into which is wrapped two or three turns of floss 26, which locks the floss 26 to holder 20. Holder 20 is held in one hand, and a holder 10 as described above is held in the other hand. The thumbs and index fingers are free to guide the floss.

Both of the embodiments described above provide numerous advantages. They are durable, long-lasting and resistant to breakage. The floss is easy to secure to and release from the holder. Less floss is used than when the floss is wrapped around the fingers. In addition, blood circulation to the fingers is not interrupted with possible circulation damage to the tips of the fingers, and the discomfort of floss wrapped tightly around the fingers is avoided. The holders are small and easy to hold, and are easily and effectively washed after each use.

A floss holder and floss holder assembly is described above. Various details of the invention may be changed without departing from its scope. Furthermore, the foregoing description of the preferred embodiment of the invention and the best mode for practicing the invention are provided for the purpose of illustration only and not for the purpose of limitation--the invention being defined by the claims.

I claim:

1. A dental floss holding assembly comprising a pair of holders, one each for being held in a hand while dental floss suspended under tension therebetween is manipulated in dental interstices, each of said pair of holders comprising:
   (a) a compact, hand-holdable substantially cylindrical member having a size for being held in and completely enclosed within the palm of the hand;
   (b) said hand-holdable member having positioned on the cylinder wall intermediate the ends an outwardly-extending disk defining a floss-retaining groove between said hand-holdable member and said disk for securing one wrapped end of said length of floss therearound, said disk having a diameter approximately one-half the length of the hand-holdable member.

2. A dental floss holding assembly according to claim 1, wherein said pair of holders are identical.

3. A dental floss holding assembly according to claim 1, wherein said member and said disk are integrally-formed of a moldable plastic material.

4. A dental floss holding assembly according to claim 1 or 3, wherein said member comprises a solid cylinder shape.

5. A dental floss holding assembly according to claim 4, wherein said disk is positioned on an axially-extending cylindrical side wall of said member at substantial right angles thereto.

6. A dental floss holding assembly according to claim 5, wherein said disk has a diameter no greater than the diameter of said member.

7. A dental floss holding assembly according to claim 5, wherein said disk has a diameter no less than the diameter of said member.

8. A dental floss holding assembly according to claim 1 or 3, wherein said groove decreases in width towards a post by which the disk is attached to the member.

* * * * *

UNITED STATES PATENT AND TRADEMARK OFFICE
CERTIFICATE OF CORRECTION

PATENT NO. : 4,926,820
DATED : May 22, 1990
INVENTOR(S) : F. Stafford Wearn

It is certified that error appears in the above-identified patent and that said Letters Patent are hereby corrected as shown below:

Column 2, line 56, correct "13" to read --12--.

Signed and Sealed this

Twenty-third Day of July, 1991

Attest:

HARRY F. MANBECK, JR.

*Attesting Officer*       *Commissioner of Patents and Trademarks*